United States Patent [19]
Ziegler

[11] 4,187,610
[45] Feb. 12, 1980

[54] IMPACTED TOOTH LIGATION CHAIN

[76] Inventor: Thomas F. Ziegler, 6924 Old Chapel Dr., Cincinnati, Ohio 45244

[21] Appl. No.: 877,305

[22] Filed: Feb. 13, 1978

Related U.S. Application Data

[63] Continuation-in-part of Ser. No. 675,547, Apr. 9, 1976, abandoned.

[51] Int. Cl.² .................................................. A61C 7/00
[52] U.S. Cl. .......................................... 433/24; 433/18
[58] Field of Search ................. 32/40 R, 14 A, 14 E, 32/14 C, 43, 42, 41, 44, 45, 61, 62

[56] References Cited

U.S. PATENT DOCUMENTS

| | | | |
|---|---|---|---|
| 1,310,654 | 7/1919 | Grimm | 32/11 |
| 2,705,367 | 4/1955 | Berke | 32/14 A |
| 3,803,715 | 4/1974 | Wallshein | 32/14 A |
| 3,835,538 | 9/1974 | Northcutt | 32/14 E |

*Primary Examiner*—Robert Peshock
*Attorney, Agent, or Firm*—Wood, Herron & Evans

[57] ABSTRACT

Disclosed herein is an impacted tooth ligation chain having at one end a tooth loop to encircle the impacted tooth and between such loop and its other end a plurality of eyelets. In practice, the tooth encircling loop is slipped around the impacted tooth crown after surgically exposing it by removing a flap of tissue. After tightening the loop about the tooth and surgically closing the wound, a ligature elastic thread is secured to an eyelet of the ligation chain, tensioned, and then secured to a bracket or arch wire in the patient's mouth.

3 Claims, 6 Drawing Figures

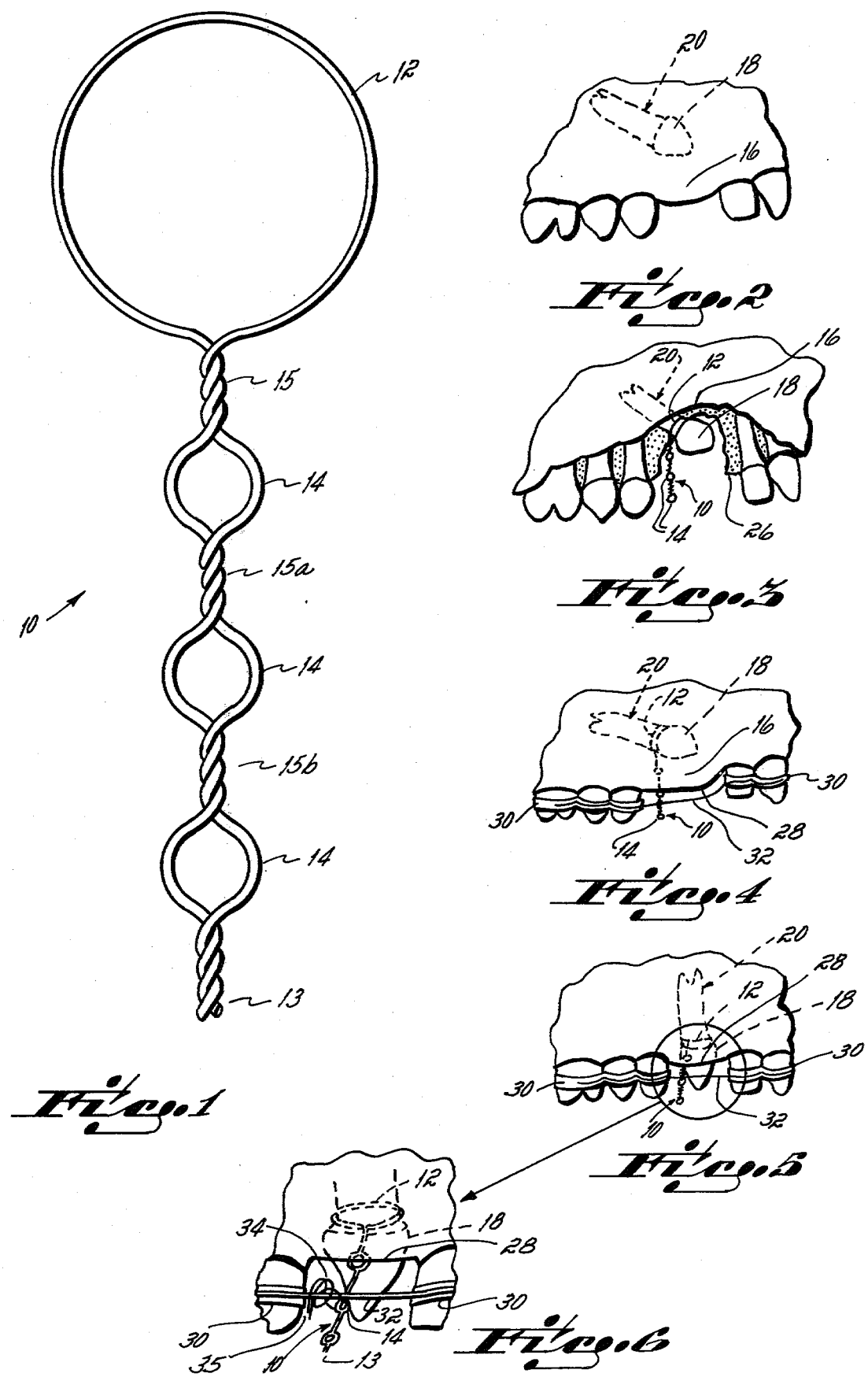

IMPACTED TOOTH LIGATION CHAIN

CROSS-REFERENCES TO RELATED APPLICATIONS

This application is a continuation-in-part of U.S. Patent Application Ser. No. 675,547, filed Apr. 9, 1976 and now abandoned, and entitled "The Impacted Tooth Ligation Chain."

BACKGROUND OF THE INVENTION

The treatment of unerupted teeth, primarily the maxillary canines, has always been a challenge to both the orthodontist and the oral surgeon. It has been recognized that the maxillary canine follows a more difficult and tortuous path of eruption than any other tooth. Because of this, normal eruption frequently does not occur and the canine becomes impacted in a labial or palatal position. In treating this problem, various methods have been tried with varying degrees of success.

A commonly employed technique is to band the impacted canine at the time of surgery. The major advantage is that after the surgical procedure the orthodontist has excellent control of the tooth, from the standpoint of both force and direction. Disadvantages include poor access, excessive bone removal, and difficulty in cementation.

Another popular technique is to expose the impacted canine surgically, removing both bone and soft tissue. The area is then packed with a dental cement or periodontal dressing, thus keeping the wound open and allowing the tooth to erupt passively. Once it is accessible, it is banded and brought into position. The main advantage of the technique is that it is less difficult for the surgeon, while the major disadvantage is that the final result may show gingival recession and incomplete bone formation around the tooth.

A third method is to expose the tooth surgically and attach a chain or wire to the crown with pins, bonding material, or ligature wire. Advantages include conservation of bone and adequate postoperative control. Disadvantages are surgical difficulty and destruction of tooth structure.

In using ligature wire surgical exposure of the tooth has been advocated. The surgical flap gives proper access for the surgeon, and the ligature wire is very small and kind to the tissues. Once the flap is resutured, the ligature wire leads the way toward the proper eruptive path. The resutured flap is critical to proper bone formation around the erupting tooth and to proper gingival contour in the final result. This method is not without its disadvantages. Often access for passing the ligature wire around the neck of the canine is limited, particularly in older children in whom the follicle around the crown is small.

The ligature wire ends are usually just pigtailed into one solid twisted wire, which leaves the orthodontist at a disadvantage in applying the significant pull on these impacted canines which is necessary to bring them in nicely. The orthodontist must try to fashion the wire into some sort of hook on which to tie. Usually this sort of homemade bent hook gives way and greatly reduces the force that can be delivered to the tooth. It also is very uncomfortable for the patient when the orthodontist forms a hook while the wire is attached to the tooth.

There are certain physiologic principles which should be adhered to if the final orthodontic result is to show normal alveolar crest bone and normal gingival contour around an impacted canine which has been brought into the mouth. Once the apex of the tooth has fully formed, the tooth has lost most of its eruptive force and must be actively moved into the mouth. The normal eruptive pathway of a canine, if it has nothing to block it, is such that when the incisal edge breaks the gingiva at the alveolar crest it is surrounded by healthy gingiva. All bone-forming tissues would be nicely intact.

BRIEF SUMMARY OF THE INVENTION

The present invention comprises an impacted tooth ligation chain which is formed from a ligature wire. More particularly, the wire is formed and twisted in such a manner that a ligation chain is provided which has: (1) a large closed loop at one end of a sufficient diameter to encircle the anatomic crown of the impacted tooth; and (2) a plurality of smaller loops or eyelets. The smaller loops provide a means for attaching elastic ligature thread to the chain. In practice, the large loop of the ligation chain is slipped around the anatomic crown of the impacted tooth which has been surgically exposed. The chain is twisted so that the diameter of the large loop is reduced to a point where it will not slip from the tooth when tension is applied thereto. The surgical flap is then repositioned and resutured. Through the smaller exposed loop closest to the gingiva is passed an elastic ligature thread whose ends are tied securely to an anchor means such as a bracket of an adjacent tooth or an arch wire. Sufficient tension on the ligation chain is provided by tensioning the elastic ligature so as to provide a force sufficient to erupt and/or guide the impacted tooth to a proper position. As the tooth approaches the surface of the gingival tissue, eyelets closer to the large loop will become visible and these will be used, during successive visits of the patient, to tie the chain to the bracket or arch.

The advantages of my invention over the prior art include one or more of the following, depending upon which prior art method it is compared to:

(A) The ease and speed with which my ligation chain may be securely attached to the impacted tooth;

(B) The minimum amount of bone removal that is required;

(C) The ease with which force may be applied to the impacted tooth;

(D) The ease with which the ligation chain can be periodically retensioned;

(E) The reduction of patient discomfort;

(F) The elimination of adhesives or pins to secure the ligation chain to the impacted tooth;

(G) The ease with which my ligation chain can be removed; and (H) Excellent gingival contour and proper clinical crown length.

DESCRIPTION OF THE DRAWINGS

In the drawings:

FIG. 1 is an elevational view of a ligation chain formed in accordance with the principles of this invention;

FIGS. 2-5 are diagrammatic illustrations of the method whereby an impacted tooth is treated; and FIG. 6 is an enlarged view of the encircled portion of FIG. 5.

DESCRIPTION OF THE PREFERRED EMBODIMENT

Referring to FIG. 1, the impacted tooth ligation chain 10 of the present invention will now be described. At one end of the ligation chain is a tooth loop portion 12 which is specially sized so as to be easily slipped around the tooth to be treated. Preferably the diameter of the tooth loop portion 12 is about 8 mm. Intermediate the tooth loop portion 12 and the other end 13 of the ligation chain 10 are a plurality of smaller loops 14 or eyelets. Preferably the diameter of such smaller loops is about 2 mm. Preferably there are three such eyelets 14 provided.

The impacted tooth ligation chain 10 is made from a round stainless steel ligature wire in the following manner. Such a wire, having a diameter of about 0.305 cm and a length of about 15.24 cm, is looped first at its midpoint around an 8 mm dowel. The ends are then wound over each other to make four tight twists 15 of the wire. This leaves a large tooth loop 12 with an inside diameter of about 8 mm, followed by four tight twists. After the first series of four twists, the continuous wire is then looped over a 2 mm dowel and four more tight twists 15a are made. This leaves a 2 mm (inside diameter) loop 14 or eyelet, then four more tight twists 15b, followed by a second 2 mm (inside diameter) loop 14 or eyelet. More eyelets 14 can be provided if desired. Three or four eyelets 14 are usually sufficient.

The method of using the ligation chain 10 will become apparent from a reference to FIGS. 2–6 and the following written description. An oral surgeon surgically lays a flap 16 of tissue (see FIG. 3) to uncover the anatomic crown 18 of the impacted tooth 20 and removes just enough bone to allow the tooth loop 12 of the chain 10 to be passed over the crown 18 of the tooth, past its greatest diameter. Sometimes bone will be removed from all around the tooth but most frequently only from two sides thereof. This lassoing is greatly aided by the use of a small amalgam plugger (not shown) to help direct the tooth loop 12 under the crown 18. Once the tooth loop 12 is past the greatest diameter of the crown 18, the surgeon twists the chain 10 several turns in the same direction as the twists 15 to reduce the diameter of the tooth loop 12 so that it will not slip from the tooth 20 when tension is applied. The chain is then passed in a straight line from the most advantageous side of the crown 18 to the crest of the alveolar ridge 26 where that particular tooth is supposed to erupt. The flap 16 is then repositioned and sutured (see FIG. 4). Only the end 13 of the chain and one or two eyelets 14 are now visibly extending out of the gingival tissue 28.

Once this is done, the orthodontist can place orthodontic bands 30 on all of the erupted teeth and an arch wire 32 can be placed. At this point, the orthodontist activates the force to erupt the tooth by looping a piece of medium elastic ligature thread 34 through the eyelet 14 closest to the gingiva 28 and ties both ends 35 securely to the band 30 of an adjacent tooth or to the arch wire 32. Other types of anchoring means could likewise be employed. At successive appointments, higher and higher eyelets 14 will become visible and the ligature thread 34 is repositioned, retensioned, and retied until the impacted tooth 20 becomes visible and can be banded with a conventional orthodontic band (not shown). The chain can be shortened if desired during these successive treatments.

The ligation chain 10 can be easily removed once the impacted tooth has been brought into the oral cavity far enough so that a conventional orthodontic band can be fitted. Since the chain is made from a continuous piece of wire, untwisting the chain adjacent to the tooth loop 12 will provide enough space to cut the wire. After cutting the wire a slight pull will permit it to be removed. In contrast to some other prior art techniques, this removal is very easy and patient discomfort is substantially reduced.

In actual practice the ligation chain of the present invention has proven highly successful. In a study of thirty-eight impacted maxillary canines treated using the invention described herein the shortest treatment time from ligation to banding was three months, the longest was twenty-one months and the average was ten and three-fourths months. Important also were the correct gingival contour and proper clinical crown growth.

Having thus described my invention, I claim:

1. A method of applying an eruptive force to a patient's impacted tooth comprising:
   surgically exposing the anatomic crown of the impacted tooth,
   encircling the anatomic crown with a tooth encircling loop of a ligation chain, said ligation chain comprising a wire having two ends, said wire twisted so as to provide at a position intermediate the ends thereof a tooth encircling loop, the other end of said tooth ligation chain comprising the ends of said wire, said tooth encircling loop being generally circular in shape and having a diameter greater than the anatomic crown of the impacted tooth to be erupted so that after the anatomic crown of the impacted tooth has been surgically exposed said tooth encircling loop can be placed over said crown and said chain can be secured to said tooth by twisting said wire, a plurality of eyelets formed by twisting said wire, said eyelets lying between the ends of said wire and said tooth encircling loop, said eyelets being separated from each other by twists in the wire, said eyelets providing a position for attaching a ligature thread to the ligation chain,
   twisting the chain adjacent to the anatomic crown so that the tooth encircling loop cannot slip over the tooth,
   surgically closing the wound,
   attaching a ligature thread to an eyelet of the ligation chain, and
   tensioning the ligature thread so as to apply an eruptive force on the impacted tooth.

2. The method of claim 1 wherein said ligature thread is also attached to anchor means in the patient's mouth.

3. The method of claim 2 wherein as the impacted tooth works its way toward the gingiva surface and a new eyelet of the ligation chain is exposed, the eruptive force is released, the chain is shortened and the eruptive force is reapplied by securing the ligature thread to a different eyelet.

* * * * *